United States Patent
Anderson

(10) Patent No.: US 7,761,100 B2
(45) Date of Patent: Jul. 20, 2010

(54) ULTRA-LOW FREQUENCY ELECTROMAGNETIC TRACKING SYSTEM

(75) Inventor: Peter Traneus Anderson, Andover, MA (US)

(73) Assignee: General Electric Co., Schenectady, NY (US)

( * ) Notice: Subject to any disclaimer, the term of this patent is extended or adjusted under 35 U.S.C. 154(b) by 943 days.

(21) Appl. No.: 11/457,732

(22) Filed: Jul. 14, 2006

(65) Prior Publication Data

US 2006/0247511 A1 Nov. 2, 2006

Related U.S. Application Data

(63) Continuation-in-part of application No. 10/611,112, filed on Jul. 1, 2003, now Pat. No. 7,158,754.

(51) Int. Cl.
*H04W 24/00* (2009.01)

(52) U.S. Cl. .............. 455/456.1; 455/40; 455/41.1; 455/41.2; 455/456.3; 455/456.5; 455/456.6; 600/407; 600/420; 600/422; 600/424; 340/539.12; 340/539.13; 340/539.15

(58) Field of Classification Search ........ 455/41.1–41.3, 455/556.1–556.2, 456.1, 456.3, 456.5, 456.6, 455/40; 600/407, 410–417, 420–430; 340/539.12, 340/539.13, 539.15, 573.1
See application file for complete search history.

(56) References Cited

U.S. PATENT DOCUMENTS

| | | | |
|---|---|---|---|
| 4,710,708 A | 12/1987 | Rorden et al. | |
| 4,849,692 A | 7/1989 | Blood | |
| 4,945,305 A | 7/1990 | Blood | |
| 5,245,307 A | 9/1993 | Klaus et al. | |
| 5,377,678 A * | 1/1995 | Dumoulin et al. | 600/424 |
| 5,787,886 A * | 8/1998 | Kelly et al. | 600/407 |
| 6,073,045 A | 6/2000 | Dyson et al. | |
| 6,172,499 B1 | 1/2001 | Ashe | |
| 6,226,547 B1 | 5/2001 | Lockhart et al. | |
| 6,374,131 B1 | 4/2002 | Tomita et al. | |
| 6,774,624 B2 | 8/2004 | Anderson et al. | |
| 6,833,814 B2 * | 12/2004 | Gilboa et al. | 342/448 |
| 6,947,788 B2 * | 9/2005 | Gilboa et al. | 600/435 |
| 7,015,859 B2 | 3/2006 | Anderson | |
| 2001/0026244 A1 * | 10/2001 | Ieda et al. | 343/867 |
| 2005/0003757 A1 | 1/2005 | Anderson | |

OTHER PUBLICATIONS

Raab et al. (Signal Processing for Through-the-Earth Radio Communication, IEEE Transactions on Communications, col. 43, No. 12, Dec. 1995).*

* cited by examiner

*Primary Examiner*—Tuan A Tran

(57) ABSTRACT

Described herein are one or more implementations for an electromagnetic (EM) position and orientation tracking system operating at an ultra-low frequency, which reduces the strength of eddy currents produced by nearby field-distorting electrically-conductive materials ("distorters"). This effectively reduces the overall distorting effect of distorters.

21 Claims, 3 Drawing Sheets

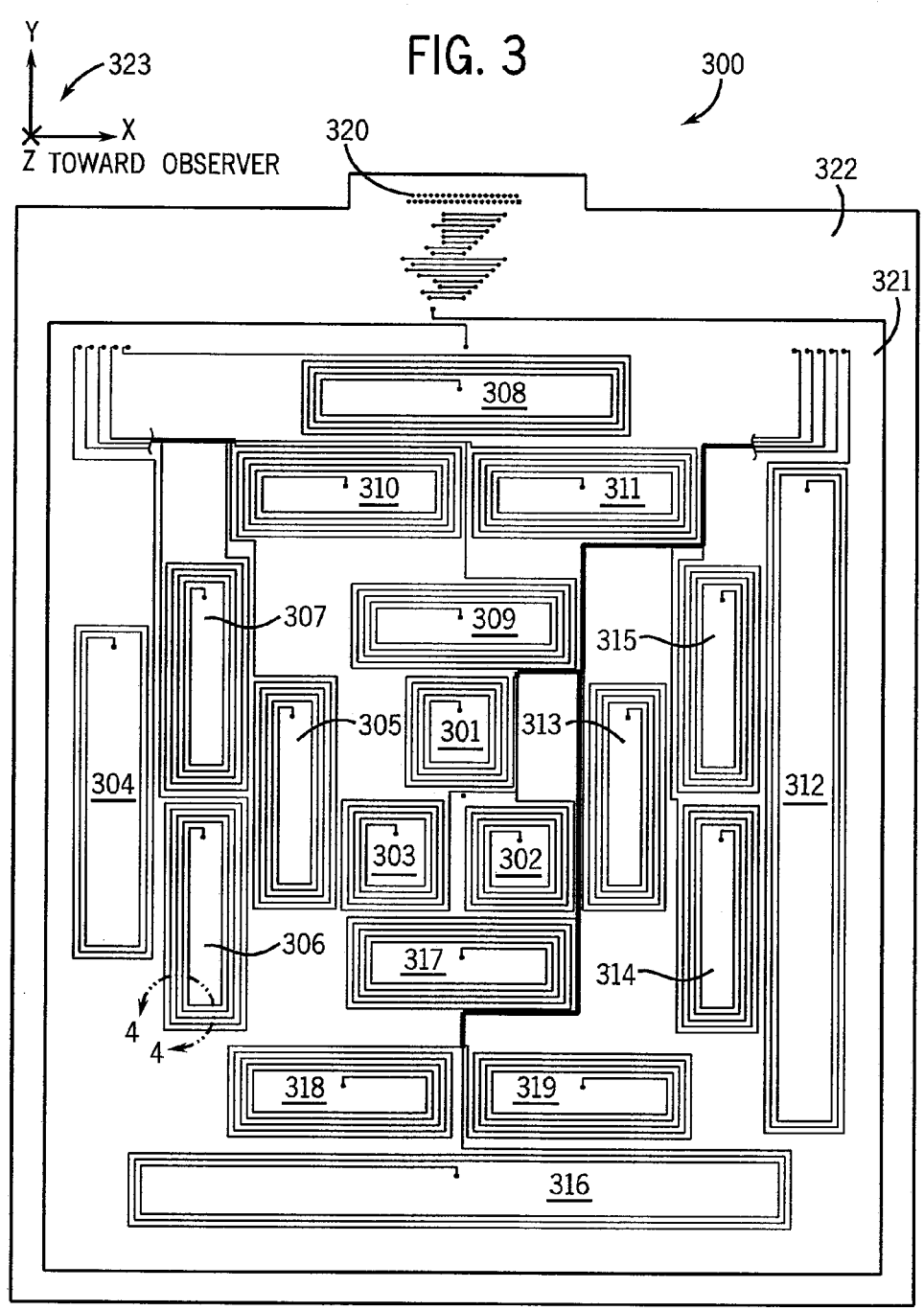

ULTRA-LOW FREQUENCY ELECTROMAGNETIC TRACKING SYSTEM

CROSS-REFERENCE TO RELATED APPLICATIONS

This application is a continuation-in-part of and claims priority to U.S. patent application Ser. No. 10/611,112, filed Jul. 1, 2003 (U.S. Publication No. 20050003757, published Jan. 6, 2005), the disclosure of which is incorporated herein by reference.

BACKGROUND OF THE INVENTION

The present invention relates generally to an electromagnetic (EM) tracking system, and more particularly to, an EM position and orientation tracking system operating at an ultra-low frequency.

Many medical procedures involve a medical instrument, such as a drill, catheter, scalpel, scope, stent or other tool. In some cases, a medical imaging or video system may be used to provide positioning information for the instrument, as well as visualization of an interior of a patient. Typically, during the course of a procedure, an instrument is guided by continuously obtaining and viewing x-ray images that show the current location of the instrument along with a portion of the patient's anatomy in a region of interest. However, because repeated exposure to x-ray radiation is harmful to medical personnel that perform image guided procedures on a daily basis, many navigation systems have been proposed that attempt to reduce exposure to x-ray radiation during the course of a medical procedure.

For example, electromagnetically tracking the position and orientation of medical instruments during a medical procedure is used as a way to decrease exposure to x-ray radiation by decreasing the number of x-ray images acquired during a medical procedure. Typically, an electromagnetic tracking system employs a transmitter and a receiver. The transmitter emits at least one signal at a frequency that is picked up by the receiver. The signal(s) from the transmitter is/are received at the receiver and the tracking system calculates position and orientation information for the medical instrument with respect to the patient or with respect to a reference coordinate system. During a medical procedure, a medical practitioner may refer to the tracking system to ascertain the position and orientation of the medical instrument when the instrument is not within the practitioner's line of sight.

The tracking or navigation system allows the medical practitioner to visualize the patient's anatomy and track the position and orientation of the instrument. The medical practitioner may then use the tracking system to determine when the instrument is positioned in a desired location. Thus, the medical practitioner may locate and operate on a desired or injured area while avoiding other structures with less invasive medical procedures.

EM position and orientation tracking systems typically contain one or more transmitters, one or more receivers, electronics to measure the mutual inductances between the transmitters and receivers, and a mechanism to calculate the position and orientation of the receivers with the respect to the transmitters.

EM position and orientation tracking systems commonly employ the industry-standard coil architecture (ISCA). ISCA uses three co-located orthogonal quasi-dipole transmitters and three co-located quasi-dipole receivers. Other systems may use three large, non-dipole, non-collocated transmitters with three collocated quasi-dipole receivers. Another tracking system architecture uses six or more transmitters spread out in space and one or more quasi-dipole receivers. Alternatively, a single quasi-dipole transmitter may be used with six or more receivers spread out in space. Alternatively still, a tracking system may use a single transmitter and a single receiver.

Conventional alternating-current (AC) based EM position and orientation tracking systems generally operate at frequencies between 8 kHz and 40 kHz. More specifically, 14 kHz is a common frequency. Other conventional EM position and orientation tracking systems, such as those described in U.S. Pat. Nos. 4,849,692 and 4,945,305, employ pulsed-direct-current "pulsed-DC" magnetic fields. These pulsed-DC tracking systems typically operate at lower frequencies than AC based EM position and orientation tracking systems.

The lower the operating frequency of an EM position and orientation tracking system the slower or less frequently measurement (e.g., position and orientation) updates occur. In addition, as the low operating frequency approaches the typically frequency of the ubiquitous AC electrical power that is supplied by the typical power utilities, typically 50-60 Hz, the magnetic fields and low harmonics of the utility power distorts the measurements.

In addition, for very electrically conductive materials, the conventional low frequencies are not low enough to make the skin depth large compared to the material's typical thickness, so these trackers experience field distortion and inaccurate tracking.

BRIEF DESCRIPTION OF THE INVENTION

Described herein are one or more implementations for an electromagnetic (EM) position and orientation tracking system operating at an ultra-low frequency, which reduces the strength of eddy currents produced by nearby field-distorting electrically-conductive materials ("distorters"). This effectively reduces the overall distorting effect of distorters.

This summary itself is not intended to limit the scope of this patent and the appending claims of this patent. Moreover, the title of this patent is not intended to limit the scope of this patent. For a better understanding of the present invention, please see the following detailed description and appending claims, taken in conjunction with the accompanying drawings. The scope of the present invention is pointed out in the appending claims.

BRIEF DESCRIPTION OF THE DRAWINGS

The same numbers are used throughout the drawings to reference like elements and features.

FIG. 3 is an example coil array that may be used in accordance with an embodiment of the present invention.

DETAILED DESCRIPTION OF THE INVENTION

Figure 1:
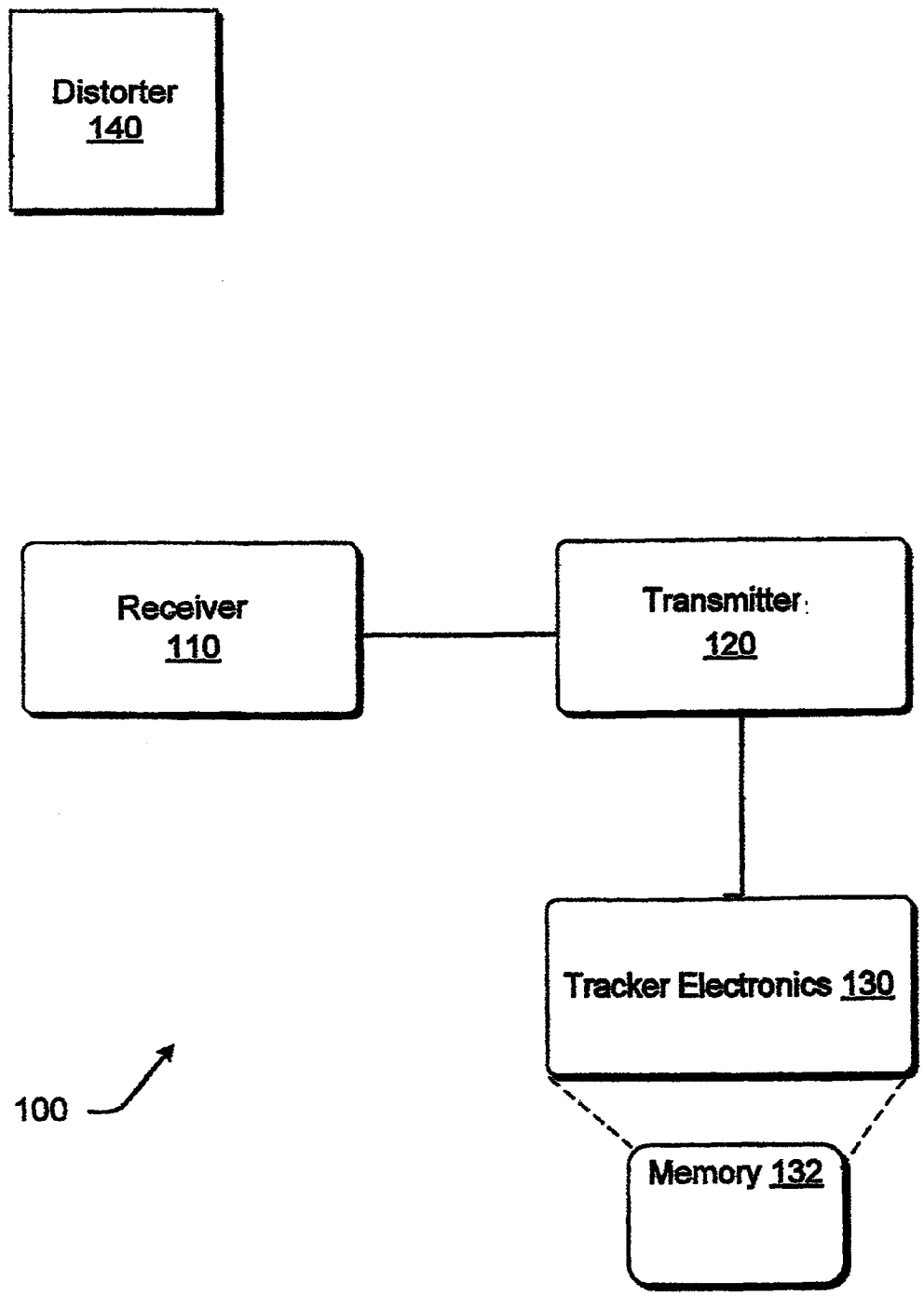
FIG. 1 is a block diagram of an electromagnetic (EM) tracking system in accordance with one or more implementations described herein.

One or more implementations, described herein, are for an electromagnetic (EM) position and orientation tracking system operating at an ultra-low frequency, which reduces the strength of eddy currents produced by nearby field-distorting electrically-conductive materials ("distorters"). This effectively reduces the overall distorting effect of distorters.

By reducing eddy-current distortion, electromagnetic (EM) position and orientation tracking may be accomplished under distortion-prone conditions. In particular, those distortion-prone conditions include the presence of one or more distorters, which produce significant distortion. More particularly still, those conditions include the presence of one or more distorters with a relatively thick "skin depth." For example, relatively thick "skin depth" includes depths greater than 0.165 inch for aluminum and 0.64 inch for titanium.

Exemplary Eddy Currents and Skin-Depth of Distorters

Electrically conductive materials ("distorters") in the vicinity of a coil arrays tend to distort the electromagnetic fields of the transmitters or receivers. This is because the varying field induces eddy currents in the distorters. This leads to inaccurate tracking. The strength of the eddy currents is less at lower frequencies.

The eddy currents act to prevent the magnetic field penetrating the distorters. Examples of common distorters include metals such as aluminum, copper, cobalt chrome, iron, and titanium. How far the magnetic field penetrates the electrically conductive material is characterized by the material parameter "skin depth". Skin depth is inversely proportional to the square root of the frequency of the magnetic field.

The skin depth is given by:

skin_depth=sqrt(2rho/(wmu))

where:
w=angular frequency=2 pi F
F=frequency in Hz
mu=magnetic permeability of the material
rho=electrical resistivity of the material Thus:

skin_depth=sqrt(2/(2pi$F$mu$c$))

skin_depth=sqrt(1/(pi$F$mu$c$))

where:
F=frequency
w=2 pi F=angular frequency
c=electric conductivity=1/resistivity
mu=magnetic permeability Thus:

$$\text{skin\_depth} = sqrt\left(\frac{\text{resistivity}}{pi\ Uo}\right) * sqrt\left(\frac{1}{F}\right) \qquad \text{Equation 1}$$

Using above information and equation, one may calculate the skin depth of, for example, aluminum and titanium.

For aluminum:

resistivity=2.8$e$-8 ohms*$M$ mu=$Uo$=permeability of free space=pi*4$e$-7$TM/A$ skin_depth=84 millimeters*sqrt(Hz)*sqrt(1/$F$)

For titanium:

resistivity=4.2$e$-7 ohms*$M$ mu=$Uo$=permeability of free space=pi*4$e$-7$TM/A$ skin_depth=326 millimeters*sqrt(Hz)*sqrt(1/$F$)

Skin depth at various frequencies:

TABLE A

Frequency and skin-depth of Aluminum

| | |
|---|---|
| 25 Hz | 16.8 millimeters = 0.66 inch |
| 100 Hz | 8.4 millimeters = 0.33 inch |
| 400 Hz | 4.2 millimeters = 0.165 inch |
| 1600 Hz | 2.1 millimeters = 0.082 inch |
| 14000 Hz | 0.71 millimeters = 0.028 inch |

TABLE B

Frequency and skin-depth of Titanium

| | |
|---|---|
| 25 Hz | 65.2 millimeters = 2.57 inches |
| 100 Hz | 32.6 millimeters = 1.28 inches |
| 400 Hz | 16.3 millimeters = 0.64 inch |
| 1600 Hz | 8.1 millimeters = 0.32 inch |
| 14000 Hz | 2.76 millimeters = 0.109 inch |

Conventional alternating-current (AC) based EM position and orientation tracking systems generally operate at frequencies between 8 kHz and 40 kHz. More specifically, 14 kHz is a common frequency. At this frequency, the skin depth of aluminum is 0.71 millimeters and the skin depth of titanium is 2.76 millimeters.

Other conventional EM position and orientation tracking systems, such as those described in U.S. Pat. Nos. 4,849,692 and 4,945,305, describe operating with pulsed-direct-current "pulsed-DC" magnetic fields. For a pulsed-DC tracking systems operating at 400 Hz, the skin depth of aluminum is 0.165 inch. Thus, aluminum thicker than 0.165 inch distorts the magnetic fields and makes tracking inaccurate.

The one or more implementations, described herein, are an EM position and orientation tracking system operating at an ultra-low frequency. In particular, the ultra-low frequency is below the ubiquitous AC electrical power that is supplied by the typical power utilities, typically 50-60 Hz, the magnetic fields and low harmonics of the utility power distorts the measurements. More particularly, the ultra-low frequency is below 60 Hz. More particularly still, the ultra-low frequency is approximately 25 Hz. At approximately 25 Hz, distortion-free measurements may be made in the presence of distorter with a skin depth approximately 0.66 inch for aluminum and 2.57 inch for titanium.

Exemplary EM Tracking System

FIG. 1 illustrates an exemplary electromagnetic (EM) position and orientation tracking system ("tracker") 100 used in accordance with one or more embodiments described herein. The tracker 100 includes at least one transmitter 120, at least one receiver 110, and tracker electronics 130. The tracker electronics 130 may include a computer or some other computational device. The various methods and procedures described herein are performed by the tracker electronics 130.

The tracker electronics 130 includes at least one memory 132, which may be any available processor-readable media that is accessible by the tracker electronics 130. The memory 132 may be either volatile or non-volatile media. In addition, it may be either removable or non-removable media.

Just to show the context, FIG. 1 shows a distorter 140 in the presence of the other components of the tracker 100. This distorter may distort the fields and thus skew the measurement of the position and orientation of the at least one transmitter 120.

The at least one transmitter 120 emits at least one transmitter signal. The at least one receiver 110 detects the at least one transmitter signal. The tracker electronics 130 analyzes the signals received by the at least one receiver 110 to determine a position of the at least one transmitter 120.

In at least one described embodiment, the at least one transmitter 120 may be a coil array of one or more coils. In at least one described embodiment, the at least one transmitter 120 is a single-coil transmitter. In at least one described embodiment, the at least one transmitter 120 is a multiple-coil transmitter. The at least one transmitter 120 may be a battery-powered wireless transmitter, a passive transmitter, or a wired transmitter. The at least one transmitter 120 may be powered by a direct current (DC) or an alternating-current (AC) power source. In at least another described embodiment, the receiver 110 may be a coil array of one or more coils. In at least one described embodiment, the receiver 110 is a single-coil receiver. In at least one described embodiment, the receiver 110 is a multiple-coil receiver. The at least one receiver 110 may be a battery-powered wireless receiver, a passive receiver, or a wired receiver. The at least one receiver 110 may be powered by a DC or an AC power source.

In at least one embodiment, the at least one transmitter 120 is a single transmitter which is driven by a sine wave at one frequency. The single transmitter gives five degrees of freedom of tracking, as transmitter roll cannot be tracked.

If roll information is desired, then the at least one transmitter 120 may include a second transmitter, which is fixed with respect to a first transmitter. The axes of the two transmitters are pointed in different directions, and optimally although not necessarily, approximately perpendicular to one another. One of the transmitters is driven by a sine wave at the single frequency, and the other transmitter is driven by a cosine wave at the same single frequency.

The embodiment with at least two transmitters 120 is producing a rotating magnetic field with perhaps an amplitude dependent on the angle of rotation, which is permissible, so the roll of the transmitter assembly is encoded in the phase of the received magnetic field. Still only one frequency is being used in this embodiment.

In the embodiment with a single transmitter, the single transmitter is driven by a sine wave at a frequency below the frequency of the utility-power frequency. These lower frequencies provide a larger skin depth, permitting distortionless tracking of thicker electrically conductive materials.

To maximize the measurement speed, a frequency is chosen that is approximately half the typical utility-power frequency. This permits centering the receiver electronics passband, whether realized in hardware, firmware, or software, between 0 Hz (direct current (DC)) and the typical utility-power frequency of 50 Hz or 60 Hz. For example, the at least one transmitter 120 with a single transmitter may operate at a frequency of 25.44 Hz. Of course, other embodiments may operate at other frequencies below that of the typical utility-power frequency, such as 50 Hz, 40 Hz, 30 Hz, 25 Hz, 20 Hz, 10 Hz, or any other frequency below 60 Hz.

Using the above example of a single transmitter operating at a frequency of 25.44 Hz, the measurement period is 118 milliseconds. This means that at least one measurement may be made every 118 milliseconds. To make the system more responsive, multiple (e.g., four) time-staggered measurements may be made in the 118 millisecond measurement period simultaneously. With the example of four measurements, a new measurement is made every 118/4=29.5 milliseconds.

Methodological Implementation

Figure 2:
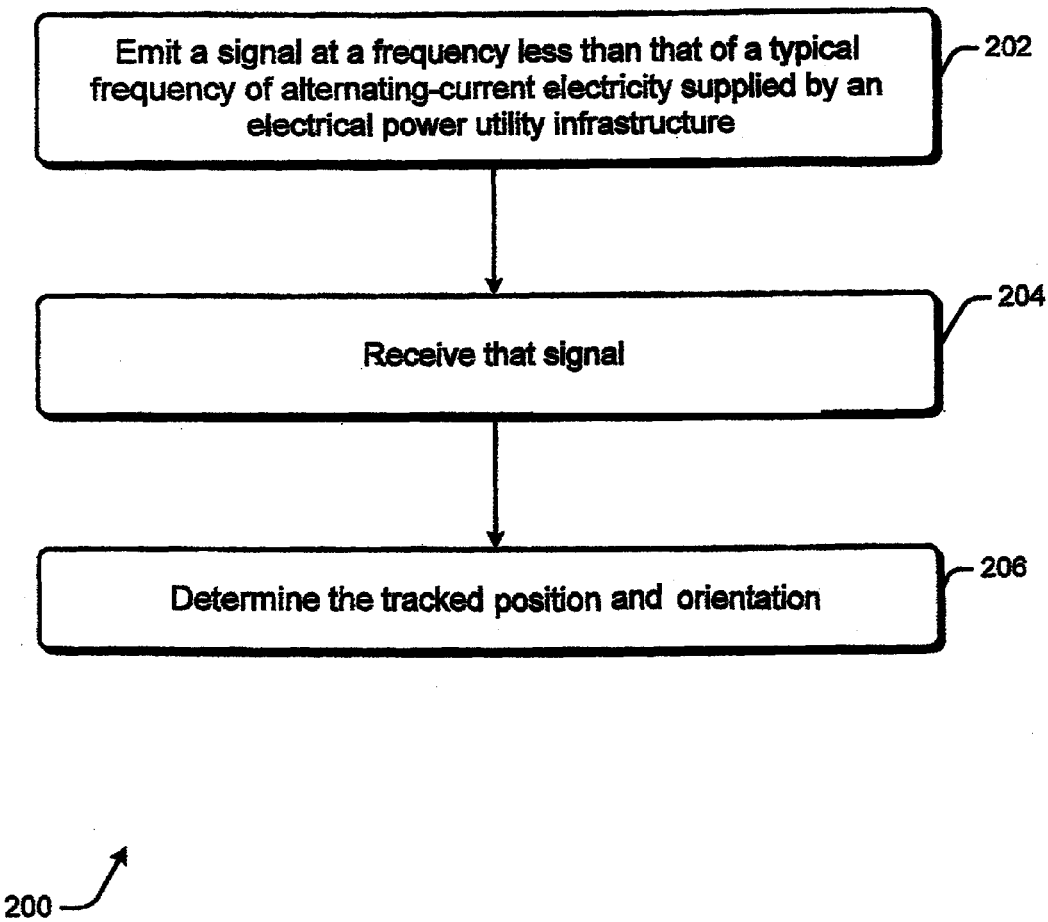
FIG. 2 is a flow diagram of a methodological implementation in accordance with one or more implementations described herein.

FIG. 2 shows a method 200 for EM position and orientation tracking at an ultra-low operating frequency. This method 200 is performed by the one or more of the various components as depicted in FIG. 1. Furthermore, this method 200 may be performed in software, hardware, or a combination thereof. For ease of understanding, this method is delineated as separate steps represented as independent blocks in FIG. 2; however, these separately delineated steps should not be construed as necessarily order dependent in their performance. Additionally, for discussion purposes, the method 200 is described with reference to FIG. 1. Also for discussion purposes, particular components are indicated as performing particular functions; however, other components (or combinations of components) may perform the particular functions.

At 202 of FIG. 2, the at least one transmitter 120 emits at least one signal at a frequency less than that of a typical frequency of AC electricity supplied by an electrical power utility infrastructure, typically 50-60 Hz.

At 204, the at least one receiver 110 receives the at least one signal from the at least one transmitter.

At 206, based upon the received at least one signal, the tracker electronics 130 determines the position and orientation of the at least one transmitter 120.

Example Coil Array

FIG. 3 is an example coil array 300 that may be used in accordance with an embodiment of the present invention. It is well known by the electromagnetic principle of reciprocity, that a description of a coil's properties as a transmitter can also be used to understand the coil's properties as a receiver. Therefore, this example coil array 300 may be used as a transmitter or a receiver.

This example coil array 300 is formed by a plurality of flat coils of straight conductor traces forming square or rectangularly-shaped spirals on a printed circuit board (PCB) 322. The spirals are preferably copper traces with spaces in-between. The spirals may be single-sided or double-sided on the PCB 322. The PCB 322 may be a two-sided single layer or multi-layer PCB. The PCB 322 includes at least one layer with conductors on one or both sides, or even on inner layers, and including a plurality of conductor through holes 320 for mounting a connector to the PCB 322. The PCB 322 may also include a plurality of additional conductor through holes within the spirals and other locations of the PCB. The PCB 322 may be made of a material that is rigid or flexible.

In an embodiment, the coil array PCB 322 includes twelve separate coils, plus a calibration coil. Four of the coils are single spirals 301, 302, 303 and 321. Eight of the coils are spiral pairs 304-312, 307-315, 306-314, 305-313, 311-319, 308-316, 310-318, and 309-317. The second spiral in each pair is wound in the opposite direction from the first spiral to from fields that are parallel to the plane of the board. The coils are arranged to generate fields and gradients in all three axis (X, Y and Z) directions at a "sweet spot" located above at least one side of the PCB 322. As shown in FIG. 3 at 323, the X and Y directions are in the plane of the PCB 322. The Z direction is perpendicular to the plane of the PCB 322. In the example shown, the "sweet spot" is located approximately 0.27 meters above at least one side of the PCB 322.

A first coil (coil 1) comprises first spiral 304 and second spiral 312. A second coil (coil 2) comprises first spiral 307 and second spiral 315. A third coil (coil 3) comprises first spiral 306 and second spiral 314. A fourth coil (coil 4) comprises first spiral 305 and second spiral 313. A fifth coil (coil 5) comprises first spiral 311 and second spiral 319. A sixth coil (coil 6) comprises first spiral 308 and second spiral 316. A seventh coil (coil 7) comprises first spiral 310 and second spiral 318. An eighth coil (coil 8) comprises first spiral 309 and second spiral 317. A ninth coil (coil 9) comprises spiral 302. A tenth coil (coil 10) comprises spiral 303. An eleventh coil (coil 11) comprises spiral 301. A twelfth coil (coil 12) comprises spiral 321. Spiral 321 (coil 12) is located around the edges or periphery of PCB 322 and thus surrounds all the other spirals.

This particular example also includes a calibration coil. The calibration coil is a thirteenth coil of one turn, laid out to provide a known small mutual inductance to each of the other coils.

The PCB 322 facilitates tracking around a small volume or "sweet spot" located above at least one side of the PCB 322. In an embodiment, the PCB provides magnetic fields in the sweet spot that are approximately as follows: a mostly uniform field pointed in the X direction; a field varying mostly with X pointed in the X direction; a field varying mostly with Y pointed in the X direction; a field varying mostly with Z pointed in the X direction; a mostly uniform field pointed in the Y direction; a field varying mostly with X pointed in the Y direction; a field varying mostly with Y pointed in the Y direction; a field varying mostly with Z pointed in the Y direction; a mostly uniform field pointed in the Z direction; a field varying mostly with X pointed in the Z direction; a field varying mostly with Y pointed in the Z direction; and a field varying mostly with Z pointed in the Z direction.

The PCB 322 utilizes an approximate nature of the "mostly uniform" fields to produce an effect of the desired "varying mostly" fields. The "mostly uniform" fields may have gradients. For example, consider the Z direction fields. The one large coil 321 generates a "mostly uniform" field in the Z direction. The three small coils 301, 302 and 303 generate smaller "mostly uniform" Z fields displaced from the main "mostly uniform" Z field generated by the large coil 321. The effects of the "mostly varying" fields may be produced by taking the sums and differences among the four fields discussed above. Fields in the X and Y directions may be generated similarly. However, connected pairs of series opposing coils 305, 306 and 307, and 313, 314, and 315 (X direction) and 309, 310 and 311, and 317, 318, and 319 (Y direction) may be used instead of single coils to generate fields in the X and Y directions. The above fields may be calculated using a straight-line segment field model, for example.

The single spiral coils 301, 302, 303 and 321 generate non-uniform fields. The non-uniform fields generated by single coils 301, 302, 303 and 321 are generated mostly in the Z direction at the "sweet spot". For the spiral pair coils 304-319, each spiral pair for each coil is connected in series. These coils produce non-uniform fields pointed mostly in the X and Y directions at the "sweet spot." For example, the coil of spiral pairs 304 and 312 on opposite edges of the PCB 322 generate a "mostly uniform" field in the X direction. Another coil of spiral pairs 308 and 316 on opposite edges of the PCB generate a "mostly uniform" field in the Y direction. The single large coil 321 generates a "mostly uniform" field mostly in the Z direction.

When the coil array board is used as a receiver array, a small current is passed through the calibration coil to provide known signals in each of the other twelve coils for calibration of the gain of the receiver electronics.

As another example, consider coils 1 through 12 as transmitters. Coils 1 through 8 each consist of first and second spirals connected in series. The first spirals and second spirals are wound in opposite directions to generate fields that are predominantly parallel to the board at the "sweet spot" positioned approximately 0.27 meters above the center of the board. Coils 9 through 12 have one spiral each, and generate fields that are predominantly perpendicular to the board at the "sweet spot" positioned approximately 0.27 meters above the center of the board.

The magnetic field can be calculated using an exact analytical result for the magnetic field due to a finite-length straight-line current segment. It is well-known from classical electromagnetics how to calculate the vector magnetic field B at any location in space due to a current I flowing in a straight-line finite-length thin wire. The vector magnetic field B contains a component Bx in the X direction, plus a component By in the Y direction, plus a component Bz in the Z direction.

For this example, values of Bx/I, By/I and Bz/I for coils 1 through 12 were calculated at approximately 0.27 meters above the center of PCB 322.

For coils 1, 2, 3, 4, Bx/I is larger in magnitude than either By/I or Bz/I, showing these coils produce a field predominantly parallel to the X axis.

For coils 5, 6, 7, 8, By/I is larger in magnitude than either Bx/I or Bz/I, showing these coils produce a field predominantly parallel to the Y axis.

For coils 9, 10, 11, 12, Bz/I is larger in magnitude than either Bx/I or By/I, showing these coils produce a field predominantly parallel to the Z axis.

Because there are significant values of all three field components, a field sensor, such as a single small coil, though other sensors could be used, approximately 0.27 meters above the center of the PCB, will receive a large signal no matter what the sensor's orientation. Of course, which coil or coils provide the large sensor signal depends on the sensor orientation, thus providing method of determining sensor orientation.

In an embodiment, the PCB 322 does not include coils with curved traces. Magnetic fields may be more precisely calculated with coils having straight-line segments.

Other Applications, Implementations, and Details

The discussion herein focuses on the specifics of a medical tracking or navigational system, especially on used to track medical instruments in a patient's anatomy. However, the details of these described specifics are merely exemplary.

The functionality of the described implementations may and can be employed in variety of applications where it is desirable to accurately track the position of items other than medical instruments in a variety of applications. That is, a tracking system may be used in other settings where the position of an instrument in an object or an environment is difficult to accurately determine by visual inspection.

For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking technology may also be used for tracking an engine inspection borescope with a low frequency electromagnetic tracking system. When inspecting the interior of a jet engine, a borescope is inserted through an inspection port. The borescope is used to inspect the blades and other interior parts of the engine for defects. For inspection purposes, the borescope operator needs to know where inside the engine the borescope is at a given time, so that any defects can be located and repaired. A low frequency electromagnetic tracking system can be used to accurately track the position and orientation of a borescope in the presence of large amounts of metal as would be found in a jet engine. This tracking system can be used to track the position and orientation of the borescope inside the engine. The system calculates and displays the borescope position and orientation within the engine.

Tracking systems are also often used in virtual reality systems or simulators. Tracking systems may be used to monitor the position of a person or object in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Recall that, by reciprocity, the mutual inductance of two transmitters/receivers is the same, whichever is the transmitter and whichever is the receiver. Therefore, unless the context indicates otherwise, the reader should understand that when transmitters and receivers are discussed herein, the relative positioning and functionality of the receivers and transmitters may be swapped. Because of mutual inductance the functionality of the implementation with swapped receivers and transmitters remains the same as an implementation where there is no swapping of the receivers and transmitters.

Furthermore, the techniques, described herein, may be implemented in many ways, including, but not limited to, medical devices, medical systems, program modules, general- and special-purpose computing systems, network servers and equipment, dedicated electronics and hardware, and as part of one or more computer networks.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

What is claimed is:

1. An electromagnetic tracking system, the system comprising:
    at least one transmitter configured to emit one or more signals at a frequency less than that of a typical frequency of alternating-current electricity supplied by an electrical power utility infrastructure;
    at least one receiver configured to receive the one or more signals from the at least one transmitter; and
    electronics configured to process the one or more signals received by the at least one receiver;
    wherein the at least one transmitter includes a first transmitter configured to emit a sine wave signal at a single frequency less than that of a typical frequency of alternating-current electricity supplied by an electrical power utility infrastructure and a second transmitter configured to emit a cosine wave signal at the same single frequency.

2. The system as recited in claim 1, wherein the at least one transmitter is further configured to emit one or more signals at a frequency below 60 Hz.

3. The system as recited in claim 1, wherein the at least one transmitter is further configured to emit one or more signals at a frequency below 50 Hz.

4. The system as recited in claim 1, wherein the at least one transmitter is further configured to emit one or more signals at a frequency below 40 Hz.

5. The system as recited in claim 1, wherein the at least one transmitter is further configured to emit one or more signals at a frequency below 30 Hz.

6. The system as recited in claim 1, wherein the at least one transmitter is further configured to emit one or more signals at a frequency of approximately 25 Hz.

7. The system as recited in claim 1, wherein the at least one transmitter is further configured to emit one or more signals at a frequency below 20 Hz.

8. The system as recited in claim 1, wherein the at least one transmitter is further configured to emit one or more signals at a frequency approximately half of that of a typical frequency of alternating-current electricity supplied by an electrical power utility infrastructure.

9. The system as recited in claim 1, wherein the at least one transmitter is powered by an alternating-current power source.

10. The system as recited in claim 1, wherein the at least one transmitter is a single-coil transmitter and the at least one receiver is a multiple-coil receiver array.

11. The system as recited in claim 1, further comprising a distorter in the presence of the at least one transmitter or the at least one receiver, the distorter not distorting the one or more emitted signals by the at least one transmitter and the one or more signals received by the at least one receiver.

12. The system as recited in claim 1, wherein the at least one transmitter is a wireless transmitter.

13. The system as recited in claim 1, wherein the at least one transmitter is a wired transmitter.

14. The system as recited in claim 1, wherein the at least one transmitter is a coil array comprised of one or more coils.

15. The system as recited in claim 1, wherein the at least one receiver is a coil array comprised of one or more coils.

16. An electromagnetic tracking system, the system comprising:
    an transmitter coil array comprised of one or more coils, the transmitter coil array configured to emit a signal at a frequency less than 60 Hz and the transmitter coil array powered by an alternating current power supply;
    a receiver coil array comprised of one or more coils, the receiver coil array being configured to receive the signal from the transmitter coil array; and
    electronics configured to process the signal received by the receiver coil array;
    wherein the transmitter coil array includes a first coil configured to emit a sine wave signal at a single frequency less than 60 Hz and a second coil configured to emit a cosine wave signal at the same single frequency.

17. The system as recited in claim 16, wherein the transmitter coil array comprises a single coil.

18. The system as recited in claim 16, wherein the transmitter coil array is tracked in position and orientation with respect to the receiver.

19. An electromagnetic tracking system, the system comprising:
    an transmitter coil array comprised of one or more coils, the transmitter coil array being configured to emit a signal at a frequency less than that of a typical frequency of alternating-current electricity supplied by an electrical power utility infrastructure;
    a receiver coil array comprised of one or more coils, the receiver coil array being configured to receive the signal from the transmitter coil array; and
    electronics configured to process the signal received by the receiver coil array;
    wherein the transmitter coil array comprises a first single-coil transmitter having an axis and a second single-coil transmitter having an axis, wherein the axis of the first single-coil transmitter is pointed in a differing direction than the axis of the second single-coil transmitter; and wherein:
a signal produced by the first single-coil transmitter is driven by a sine wave;
a signal produced by the second single-coil transmitter is driven by a cosine wave; and
the signals produced by the first single-coil transmitter and the second single-coil transmitter have the same frequency.

20. The system as recited in claim 19, wherein the transmitter coil array is driven by a sine wave at a single frequency less than the typical frequency of alternating-current electricity supplied by an electrical power utility infrastructure.

21. An electromagnetic tracking system, the system comprising:
an transmitter coil array comprised of one or more coils, the transmitter coil array being configured to emit a signal at a frequency less than that of a typical frequency of alternating-current electricity supplied by an electrical power utility infrastructure;
a receiver coil array comprised of one or more coils, the receiver coil array being configured to receive the signal from the transmitter coil array; and
electronics configured to process the signal received by the receiver coil array;
wherein the transmitter coil array comprises a first single-coil transmitter having an axis and a second single-coil transmitter having an axis, wherein the axis of the first single-coil transmitter is pointed in a differing direction than the axis of the second single-coil transmitter; and
wherein the first single-coil transmitter is driven by a sine wave at a single frequency and the second single-coil transmitter is driven by a cosine wave at the same single frequency.

* * * * *